(12) United States Patent
Guerra-Santos et al.

(10) Patent No.: US 6,936,279 B2
(45) Date of Patent: Aug. 30, 2005

(54) MICROCRYSTALLINE ZEAXANTHIN WITH HIGH BIOAVAILABILITY IN OILY CARRIER FORMULATIONS

(75) Inventors: Luis H. Guerra-Santos, Ballwin, MO (US); Dale K. Greenbury, St. Louis, MO (US)

(73) Assignee: Zeavision LLC, St. Louis, MO (US)

( * ) Notice: Subject to any disclaimer, the term of this patent is extended or adjusted under 35 U.S.C. 154(b) by 0 days.

(21) Appl. No.: 10/173,174

(22) Filed: Jun. 18, 2002

(65) Prior Publication Data

US 2003/0232892 A1 Dec. 18, 2003

(51) Int. Cl.$^7$ .................................................. A61K 9/14
(52) U.S. Cl. ...................... 424/489; 424/490; 424/491; 424/493
(58) Field of Search ................................. 424/451, 455, 424/502, 489, 490, 491, 493, 492

(56) References Cited

U.S. PATENT DOCUMENTS

| | | | |
|---|---|---|---|
| 4,522,743 A | | 6/1985 | Horn et al. |
| 4,726,955 A | | 2/1988 | Horn et al. |
| 4,851,339 A | | 7/1989 | Hills |
| 5,118,511 A | * | 6/1992 | Horn et al. .................. 424/502 |
| 5,180,747 A | | 1/1993 | Matsuda et al. |
| 5,290,605 A | | 3/1994 | Shapira |
| 5,350,773 A | | 9/1994 | Schweikert et al. |
| 5,356,636 A | | 10/1994 | Schneider et al. |
| 5,545,414 A | | 8/1996 | Behr et al. |
| 5,827,652 A | * | 10/1998 | Garnett et al. ............... 424/451 |
| 5,876,754 A | | 3/1999 | Wunderlich et al. |
| 5,968,251 A | | 10/1999 | Auweter et al. |
| 6,007,856 A | * | 12/1999 | Cox et al. .................... 426/250 |
| 6,235,315 B1 | | 5/2001 | Runge et al. |
| 6,271,396 B1 | | 8/2001 | Auweter et al. |
| 6,296,877 B1 | | 10/2001 | Auweter et al. |
| 6,372,782 B1 | | 4/2002 | Patel et al. |
| 6,406,735 B2 | | 6/2002 | Stein et al. |
| 6,444,227 B1 | | 9/2002 | Leuenberger et al. |
| 6,689,400 B2 | | 2/2004 | Majeed |

FOREIGN PATENT DOCUMENTS

| | | |
|---|---|---|
| EP | 1 066 761 A2 | 1/2001 |
| WO | WO 01/19383 A2 | 3/2001 |

* cited by examiner

*Primary Examiner*—Thurman K. Page
*Assistant Examiner*—Micah-Paul Young
(74) *Attorney, Agent, or Firm*—Patrick D. Kelly (57) ABSTRACT

Zeaxanthin (ZX) or other medically or commercially important carotenoids can be prepared in microcrystalline form, in an oily carrier liquid, to increase their bioavailability following oral ingestion. Initial processing is carried out to prepare a "rough" or "coarse-grained" carotenoid preparation containing relatively large particles of the ZX or other carotenoid, in a suitable form such as a lyophilized stable powder. The coarse-grain preparation is dissolved in a suitable solvent such as tetrahydrofuran, and mixed with a carrier liquid comprising a digestible oil (such as a vegetable oil) and an emulsifying agent. The resulting oil-and-solvent mixture is injected, along with inert gas such as nitrogen, into a vacuum chamber, where a suitable vacuum and temperature combination is used to remove the solvent in a rapid "flash" manner which does not give the carotenoid crystals time to grow larger through accretion or aggregation. This generates a microcrystalline suspension containing very small particles of the ZX or other cartenoid, in the oily liquid carrier. This product can be further processed if desired, or it can be loaded directly into watertight capsules for oral ingestion. Tests on human volunteers have confirmed that the bioavailability of this microcrystalline form is substantially higher than prior art preparations having larger particles of the carotenoid.

10 Claims, 3 Drawing Sheets

MICROCRYSTALLINE ZEAXANTHIN WITH HIGH BIOAVAILABILITY IN OILY CARRIER FORMULATIONS

BACKGROUND OF THE INVENTION

This invention relates to biochemistry and medicine, and involves zeaxanthin and other carotenoids.

Zeaxanthin (occasionally abbreviated herein as ZX) is a particular carotenoid compound that is naturally present in the "macula", a small yellow-pigmented region at the center of the retinas of humans and other mammals. As used herein, the term "zeaxanthin" includes any or all of the three stereoisomers of zeaxanthin, which are often designated as the 3R–3'R isomer (also referred to as the R—R isomer, for convenience), the S-R isomer (also known as meso-zeaxanthin), and the 3S–3'S isomer. In general, the R—R isomer is believed to be preferable, and it is the isomer generated by the *Flavobacterium multivorum* bacterial strains described below.

Abnormally low concentrations of zeaxanthin in the macula have been correlated with a retinal disease called "macular degeneration". Since this disease usually manifests late in life, it is also called "age-related macular degeneration", abbreviated as AMD (or occasionally as ARMD). To distinguish macular degeneration from several other "MD" abbreviations, "AMD" is the most commonly used acronym and abbreviation for macular degeneration.

In macular degeneration, the macula (which, as noted above, is at the center of the retina) becomes unable to function properly. This causes the person to become unable to distinguish things that are in the center of his or her field of vision. If macular degeneration continues to grow worse, it often leaves its victims effectively blind. Macular degeneration is a leading cause of blindness among the elderly.

Since zeaxanthin (like other carotenoids) is not synthesized inside any mammalian body, it must be ingested from food sources. This can pose problems, since it is present in most foods only at extremely low quantities.

It has been suspected for some years that nutritional supplements or pharmaceutical preparations containing ZX might be able to help prevent, treat, or reduce the risk or severity of macular degeneration. However, no vitamin-type ("nutraceutical") supplements have been available with anything more than very small quantities of ZX. This is due to the very low concentration of ZX in most plant sources, and to the extremely high costs and difficulties in chemically synthesizing and purifying the 3R–3'R stereoisomer of ZX.

Five U.S. patents have been issued on ZX formulations generated by fermenting a bacterial line that was discovered to synthesize the 3R–3'R stereoisomer of ZX. The parent strain of those bacteria, known as *Flavobacterium multivorum*, was deposited with the American Type Culture Collection, and was given ATCC accession number 55238; however, because of changes in classification nomenclature, that strain is referred to in the ATCC catalog as *Sphingobacterium multivorum*.

The first two such patents (U.S. Pat. No. 5,308,759, Gierhart 1994, and U.S. Pat. No. 5,427,783, Gierhart 1995) relate to the use of ZX as an additive in feeds for poultry and fish. In that mode of usage, it causes the skin and egg yolks of poultry, and the meat of salmon and certain other fish, to turn a darker color, which is more appealing to consumers. Those types of feed additives typically take the form of a cell paste or other biomass, containing the remains of killed cells, without using extensive processing to extract or purify the zeaxanthin they contain.

The other three patents, all of which relate to medical use in humans, are U.S. Pat. No. 5,747,544 (Garnett et al 1998), which discloses a method of using the 3R–3'R stereoisomer of ZX to treat or prevent macular degeneration; U.S. Pat. No. 5,827,652 (Garnett et al 1998), which discloses orally ingestible formulations; and U.S. Pat. No. 5,854,015 (Garnett et al 1998), which discloses a method of making the purified 3R–3'R stereoisomer, using bacterial fermentation. Additional information on zeaxanthin, and on macular degeneration, is contained in these three U.S. patents, and the contents and teachings of those patents are incorporated herein by reference, as though fully set forth herein.

One of the current inventors herein, Luis Guerra-Santos, was involved in that development work, and is a coinventor of the three patents on ZX formulations for human use. This current invention arose out of subsequent research and development efforts which continued after the filing of those three applications.

It also should be recognized that a purely chemical method for synthesizing the R—R stereoisomer of zeaxanthin apparently has been recently been created, by Hoffman-LaRoche. That chemically synthesized version of R—R zeaxanthin is discussed in certain documents which have been submitted by Hoffman-LaRoche to the U.S. Food and Drug Administration, and which are accessible to the public via the Internet, in the FDA website.

It is assumed and believed that the processing steps disclosed herein can be tested on any type of synthetic, fermented, or other zeaxanthin (or other carotenoid) preparation having with average particle sizes larger than a micron in diameter, using no more than routine experimentation, to determine whether these steps can be used to create a "nanoparticle" zeaxanthin or other carotenoid preparation.

As used herein, the term "nanoparticle" is used to refer to a preparation of zeaxanthin (or other carotenoid) having particle sizes that are less than 1 micron in diameter, on average. Since a micron is one-millionth of a meter (equal to one-thousandth of a millimeter), and a nanometer is one billionth of a meter (or one-thousandth of a micron), this is comparable to saying that a "nanoparticle" preparation has particle sizes that average 999 nanometers, or less, in diameter. The term "sub-micron" formulation can be used interchangeably with "nanoparticle" formulation, since both terms imply that the particles have average diameters less than a micron.

The manufacturing processes disclosed herein offer a cost-effective way to create zeaxanthin preparations which consistently fall within the definition of "nanoparticle" or "sub-micron" formulations. Although it is presumed that these "nanoparticle" formulations will offer the highest possible bioavailability, for a given weight of zeaxanthin, it should be recognized that the final choice of a desired particle size range, for large-scale commercial quantities of zeaxanthin, will depend on economics, rather than on a rigid goal of smallest possible particles, and highest possible bioavailability, regardless of cost. It may turn out that the most cost-effective manufacturing process, which generates the highest level of total retinal tissue deposition among users for the lowest total manufacturing cost, may involve zeaxanthin preparations which have average diameters somewhat higher than 1 micron, and which therefore is not a true "nanoparticle" formulation.

Accordingly, the term "microcrystalline" as used herein is somewhat broader, and includes both (i) nanoparticle carotenoid formulations, and (ii) carotenoid formulations having average particle diameters of about 10 microns or less, and preferably having average particle diameters of about 4 microns or less.

By comparison, carotenoid formulations having average particle diameters larger than about 10 microns are referred to herein as "coarse-grained" formulations. Those are deemed to be the relevant prior art herein, and the goal of this invention is to provide carotenoid formulations with significantly smaller average particle sizes (and significantly better bioavailability) than coarse-grained carotenoid formulations.

Microcrystalline zeaxanthin-in-oil formulations, which can be prepared as disclosed herein (and which include nanoparticle formulations, as one subset of the microcrystalline size range) have substantially smaller average particle sizes than the prior zeaxanthin formulations that were prepared as described in U.S. Pat. Nos. 5,747,544; 5,827,652; and 5,854,015, as cited above. Since microcrystalline zeaxanthin formulations have substantially smaller particle sizes and better bioavailability than the coarse-grain formulations previously disclosed, they offer a substantial improvement over the prior known formulations, and are useful as such.

The phrases "zeaxanthin-in-oil" and "carotenoid-in-oil" are important herein, and are intended to focus upon a significant distinction between this invention, and the prior art. Various methods have been previously disclosed for preparing carotenoids (including zeaxanthin) in either of two different forms.

One form is usually referred to as a powder, "dry powder", or "coldwater dispersible powder". These types of powdered carotenoid preparations are disclosed in various publications, such as U.S. Pat. No. 5,968,251 (Auweter et al, 1999, assigned to BASF Aktiengesellschaft). These preparations are manufactured, shipped, and stored in bulk, in powdered form. Before being packaged for retail sale, this type of powder typically is loaded into a conventional capsule (which may be made of an enteric material that will not dissolve until the capsule enters the intestines; this protects the carotenoid from acidity in the stomach). Alternately, a carotenoid powder may be mixed with a binder compound and then compressed into tablet form; if desired, such tablets may be coated with a thin layer of an enteric coating, to create a convenient dosage form commonly known as "caplets".

The other major class of carotenoid preparations in the prior art involves non-homogenous suspensions of oily droplets in aqueous phases. Depending on which types of compounds are used to sustain a non-homogenous suspension in a stable form (to prevent the oily droplets from coalescing and aggregating together, which is highly undesirable), these suspensions are usually referred to by terms such as emulsions, colloids, liposomes, micelles, etc.

By contrast, the methods and mixtures disclosed herein describe microcrystalline zeaxanthin (or other carotenoid) formulations which are suspended directly in an edible oily carrier, such as a vegetable oil. It is believed that this methodology can provide significant benefits when scaled up to commercial quantities, by combining microcrystalline particles sizes with stable yet inexpensive liquid carriers that offer several advantages. As examples of such advantages, these types of oily liquid carriers can: (i) protect the microcrystalline particles against oxidation, (ii) allow the use of relatively simple fluid-handing equipment and techniques, (iii) facilitate loading of the product into soft-gel capsules; and, (iv) eliminate or reduce the need for expensive specialized compounds that can effectively coat the carotenoid molecules, in a manner which will prevent them from clumping or coalescing.

In addition, the methods and carriers disclosed herein are believed to allow less harsh, less expensive, and easier-to-control processing steps, compared to the processing steps used to create dry powders or non-homogenous suspensions.

Also, the methods used to create the carotenoid-in-oil preparations disclosed herein are believed to pose lower risks of converting desirable isomer(s) or stereoisomer(s) of certain carotenoids (such as the 3R,3'R stereoisomer of zeaxanthin, or certain "cis" or "trans" isomers of other carotenoids) into less desirable and potentially even harmful isomers.

For these and other reasons, it is believed that microcrystalline carotenoid-in-oil preparations as disclosed herein offer potentially significant advantages over other previously disclosed types of carotenoid preparations, especially during the scale-up of manufacturing operations to create commercial quantities of certain types of carotenoids (notably including zeaxanthin).

The importance of microcrystalline (and ideally, nanoparticle) preparations is discussed in further detail, under the next subheading.

Smaller Particles, Higher Bioavailability

As is well known in the art, most carotenoids (including zeaxanthin) have very low solubility in water; they are strongly hydrophobic. Accordingly, if suspended in an aqueous solution, carotenoids droplets tend to coalesce and/or aggregate, to form larger, relatively sticky masses.

This poses a major difficulty, for carotenoids that are intended to be orally ingested as drugs or nutritional supplements. Orally-ingested carotenoids must be manufactured carefully, to ensure adequate "bioavailability".

The most common indicator of bioavailability refers to the concentration of a compound which, after oral ingestion by a human or test animal, can be detected as in circulating blood. Accordingly, terms such as "increased" (or improved, enhanced, higher, etc.) bioavailability imply that a certain quantity of an orally-ingested carotenoid will provide higher concentrations of that carotenoid, in circulating blood, if compared to a carotenoid preparation having the same weight, but lower bioavailability. Since deposition of ZX in the macular portion of the retina (at least, in patients whose maculas are suffering from a deficit of ZX) will depend heavily on blood concentrations, it is assumed that any method of generating higher concentrations of ZX in circulating blood, by using formulations with higher levels of bioavailability, will indeed leader to higher quantities will be deposited more rapidly in the retina, in patients in need of such treatment.

Alternately or additionally, zeaxanthin and lutein concentrations in the retina can be measured using any of several non-invasive optical methods, which include flicker photometry (an older and less accurate standard), spectral fundus reflectance, and laser mapping. These measuring techniques are discussed in Berendschot et al, *Investig. ophthalm. Vis. Sci.* 40: S314, 1999.

Accordingly, when zeaxanthin and/or lutein are involved, actual deposition of the administered carotenoid into the macular portion of the retina (which can then be compared to earlier baseline measurements, for the same human or animal) can also be used as an indicator of greater or lesser bioavailability, for preparations of zeaxanthin or lutein.

A general rule for carotenoids (and other hydrophobic compounds) that are to be orally ingested is this: higher levels of bioavailability will result, if smaller particle sizes are used. This is because, for a given weight of any hydrophobic substance that cannot dissolve in water, smaller particle sizes lead directly to larger exposed surface areas. As a simple numerical example, if you take a cube of material which is 1 millimeter wide, high, and long, and chop it into cubes that are 1 micron on each side, then without changing the weight or volume of that compound at all, you will increase its exposed surface area by a factor of 1000 (from 6 square millimeters, initially provided by a single cube, to 60 square centimeters of surface area, provided by a billion tiny cubes). If that material is made of an oily compound that does not dissolve in water, the increase in exposed surface area will lead to higher bioavailability.

Accordingly, if ZX is put into a microcrystalline formulation, as disclosed herein, that formulation will be more bioavailable than a "coarse-grained" formulation, and it will lead to higher quantities of actual zeaxanthin deposition in the macular portion of the retina, when orally ingested by people who need to increase ZX concentrations inside their retinas.

In reviewing the prior art, it should be recognized that large numbers of prior issued patents disclose various methods of manufacturing various hydrophobic organic compounds. Although some of these processes might be applied to zeaxanthin and other similar carotenoids, they all appear to suffer from various shortcomings and limitations which would render them substantially more expensive (and probably less effective) than the process disclosed herein. In addition, the known prior methods do not appear to be oriented toward creating compounds with the smallest possible particle size, to increase bioavailability. Instead, they appear to be predominantly concerned with creating formulations with improved handling and extended shelf-life, rather than increased bioavailability.

Figure 1:
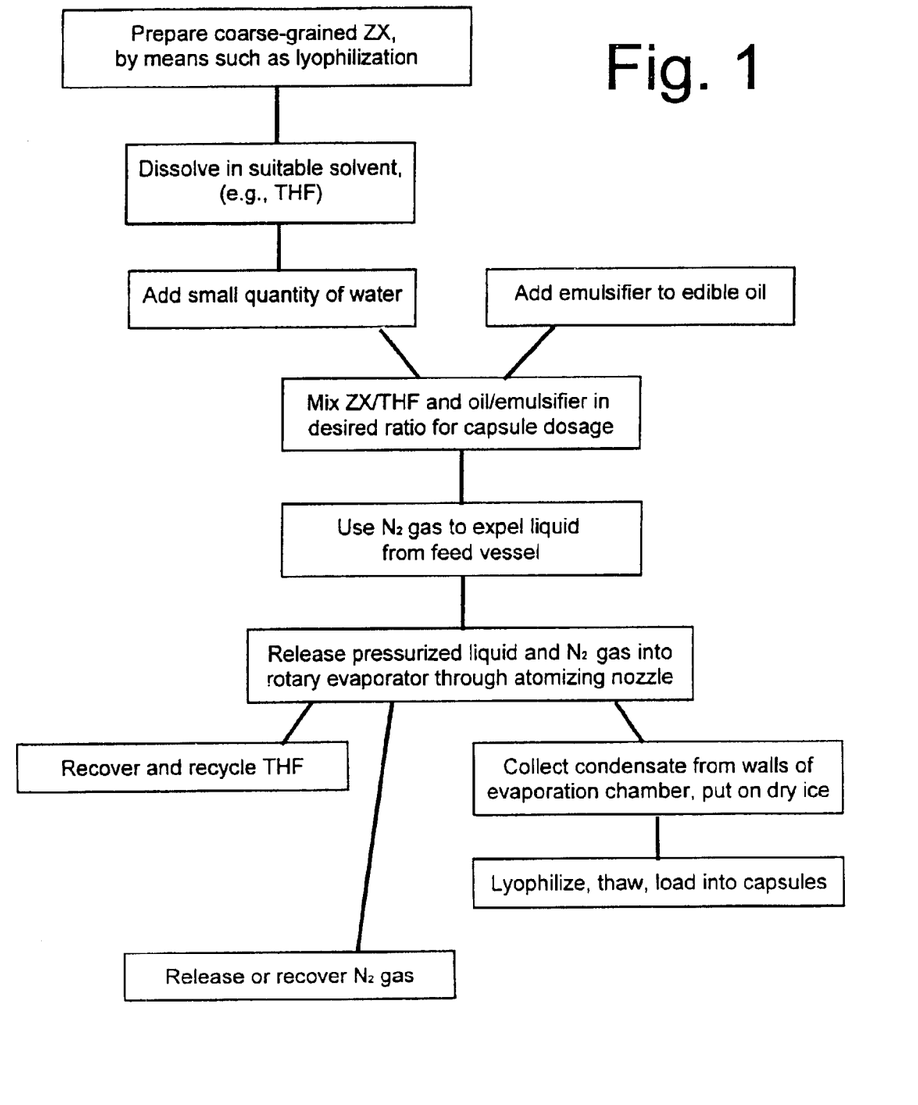
Figure 2:
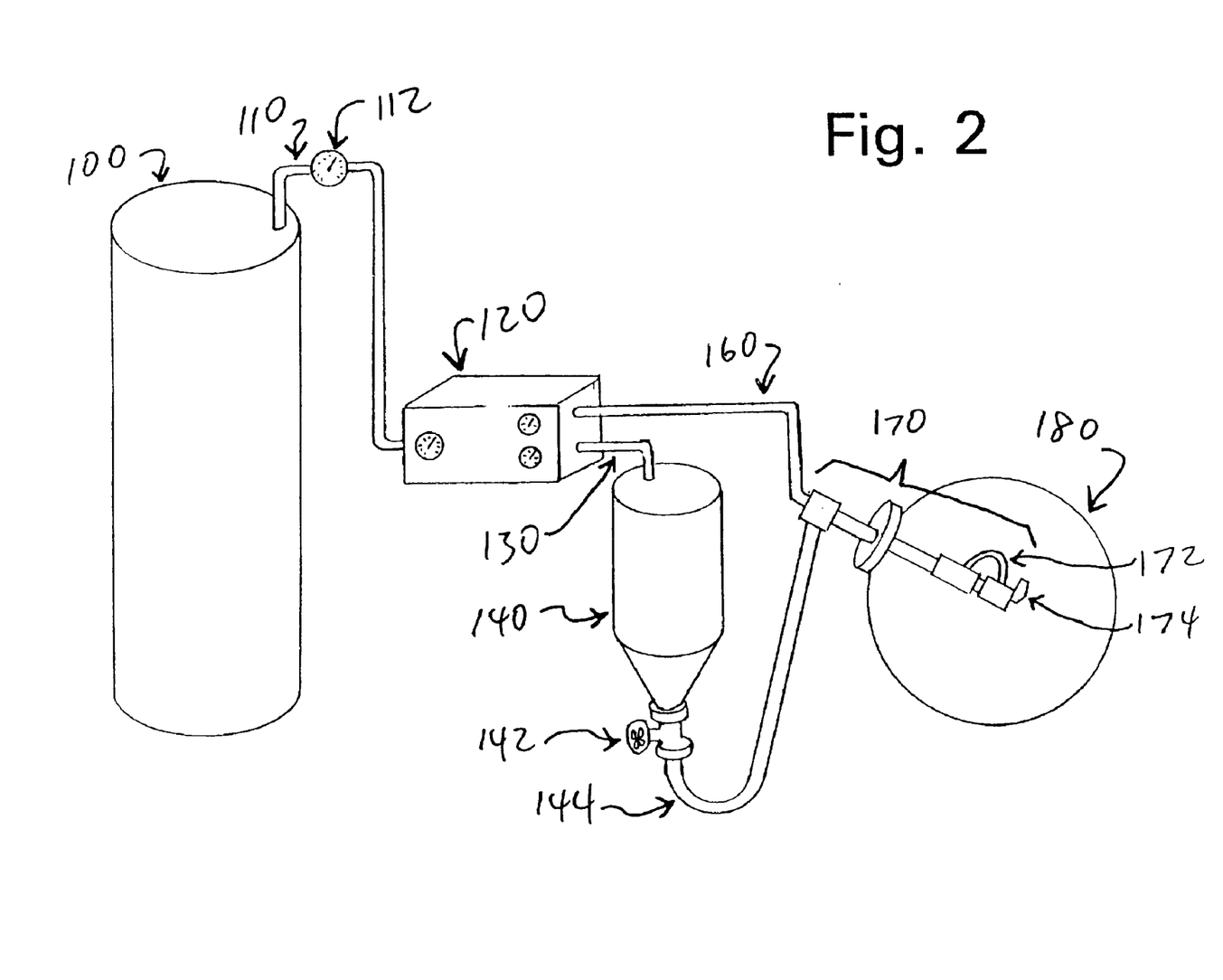

For example, U.S. Pat. No. 5,356,636 (Schneider et al 1994) discloses the use of gelatin, combined with various organic amino compounds, to create dried, powdered formulations of carotenoids and hydrophobic vitamins. U.S. Pat. No. 5,639,441 (Sievers et al, 1997) discloses methods that require the use of "supercritical" carbon dioxide (i.e., a gas which has been placed under extreme pressure, to convert it into a liquid) to generate air-borne aerosols when the solvent mixture is rapidly decompressed. U.S. Pat. No. 4,522,743 (Horn et al, 1985) requires the use of high temperatures and high pressures, the mixing of the carotenoid with a swellable colloid such as gelatin, and the precipitation of the mixture as a "colloidally dispersed" form, using a process commonly known as "flash-cooling".

Several patents issued to Haynes (including U.S. Pat. Nos. 4,725,442; 5,091,187; 5,091,188; and 5,246,707) require the use of phospholipids to create liposomes that will microencapsulate their contents. U.S. Pat. No. 5,350,773 (Schweikert et al 1994), uses glycerol and compounds such as ascorbyl palmitate to create stabilized "finely dispersed" preparations of a hydrophobic compound such as Vitamin E; however, the creation of the "finely dispersed" compound simply uses a conventional homogenizer. One other patent of lesser interest is U.S. Pat. No. 5,180,747 (Matsuda et al, 1993) which uses encapsulated vitamin preparations. These encapsulated vitamins also include a carotenoid compound in order to protect the vitamin against degradation by light.

None of these previously known methods or preparative steps can perform in the same way as the steps disclosed herein, which are relatively simple, inexpensive, and suited to commercial-scale manufacturing operations.

Accordingly, one object of this invention is to disclose an improved method for manufacturing zeaxanthin (or other carotenoids) in microcrystalline form, in an oily carrier liquid such as a vegetable oil. These microcrystalline preparations (as defined and used herein, this term refers to zeaxanthin crystals or particles having diameters less than about 10 microns, on average; preferably, these diameters are less than about 4 microns on average) have improved bioavailability, compared to other known preparations under the prior art, and the oily carrier provides them with various manufacturing and other advantages.

Another object of this invention is to disclose a process for manufacturing microcrystalline ZX with improved bioavailability, using a relatively simple and inexpensive processing step that is well-suited for commercial-scale manufacturing.

Another object of this invention is to disclose improved ZX formulations which, when orally ingested, provide higher levels of bioavailability than prior known preparations. These formulations are designed to increase the potency and efficacy of ZX in treating or preventing vision problems such as macular degeneration.

Another object of the subject invention is to disclose improved formulations containing zeaxanthin, lutein, or other carotenoids in microcrystalline form, for use as additives in feeds for poultry, salmonid fish, etc. The increased levels of bioavailability of these carotenoid in such formulations allows lower quantities to be used to achieve the desired results, and thereby increases the cost-effectiveness and reduces the total cost of carotenoid additives in animal feeds.

In addition, another object of this invention is to disclose an improved method for commercial-scale manufacturing of other carotenoids which are similar in various respects to zeaxanthin (such as beta-carotene, lycopene, astaxanthin, lutein, etc.), in a microcrystalline form (having particle sizes less than about 4 microns on average) and in an oily carrier liquid, to increase the bioavailability of the microcrystalline carotenoids compared to prior known preparations.

These and other objects of the invention will become more apparent through the following summary, drawings, and description of the preferred embodiments.

SUMMARY OF THE INVENTION

Zeaxanthin (ZX) or other medically or commercially important carotenoids can be prepared in microcrystalline form, in an oily carrier liquid, to increase their bioavailability following oral ingestion. Initial processing is carried out to prepare a "rough" carotenoid preparation, in a suitable form such as a lyophilized stable powder, containing relatively large particles of the ZX or other carotenoid. The "rough" preparation is dissolved in a suitable solvent, such as tetrahydrofuran, and mixed with a carrier liquid which comprises a digestible oil (such as a vegetable oil) and an emulsifying agent. The resulting oil-and-solvent mixture is injected, along with inert gas, into a vacuum chamber, where a combination of a suitable vacuum and temperature is used to remove the solvent in a rapid ("flash") manner, which does not give the carotenoid crystals time to grow larger through accretion or aggregation. This generates a microcrystalline suspension containing very small particles of the ZX or other carotenoid, in the oily liquid carrier. This product can be further processed if desired, or it can be loaded directly into watertight capsules for oral ingestion. Tests on human volunteers have confirmed that the bioavailability of this microcrystalline form is substantially higher than prior art preparations having larger particles of the carotenoid.

BRIEF DESCRIPTION OF THE DRAWINGS

FIG. 1 is a flow chart depicting the steps used to convert a ZX preparation having large particles, prepared by lyophilization, into microcrystalline ZX suspended in olive oil.

FIG. 2 is a schematic depiction of the main components used to feed a liquid mixture containing large-grained ZX (dissolved in solvent and mixed with an oily carrier) into a rotary evaporator.

FIG. 3 is a depiction of a solvent recovery system used in conjunction with the rotary evaporator.

DETAILED DESCRIPTION

The processing steps of this invention are depicted in a flow chart in FIG. 1, and are described in detail in Example 2. For convenience, the "upstream" (feed) vessels that were used to mix and prepare the ingredients that were injected into a rotary evaporator 180 are depicted in FIG. 2. The "downstream" vessels that were used to recover the THF solvent and nitrogen gas, after they emerged from rotary evaporator 180, are depicted in FIG. 3.

In the embodiments disclosed herein, processing was carried out on zeaxanthin preparations containing relatively large and coarse grains (ZX grains are also referred to interchangeably herein as crystals). ZX is regarded herein as an exemplary carotenoid, since it has become of substantial interest for use in preventing or treating macular degeneration in humans. It is generally believed that any comments and teachings herein regarding the methods used to prepare "microcrystalline" ZX can also be adapted for preparing "microcrystalline" forms of various other valuable carotenoids, including lutein, beta-carotene, astaxanthin, lycopene, etc. The suitability (and adaptability) of these methods for processing other such carotenoids can be evaluated by those skilled in the art, using no more than routine experimentation.

The ZX preparations used as starting materials in those tests were in a powdered lyophilized form, prepared as described in Example 1. In these coarse-grain preparations, the ZX grains typically had diameters ranging from about 10 microns to about 100 microns (micrometers, or $\mu$m). After the microcrystalline processing had been completed, the treated ZX grains had been reduced to typical size ranges of about 0.2 to about 2 $\mu$m.

As used herein, terms such as particle size, diameter, width, etc. are not meant to imply that these crystals have spherical or nearly spherical shapes. Instead, as is commonly used by those who work with microscopic crystals, these terms refer to the width of a particle, measured at the widest point, where the width is typically deemed to be the direction which is generally perpendicular to the longest axis and/or dominant grain direction of the crystal. Accordingly, terms such as diameter or width, as used herein, are generally equivalent to the diameter of a cylinder, rather than a sphere.

In the initial processing step, as shown in the flow chart of FIG. 1, the coarse-grained ZX preparation was dissolved in a suitable solvent. For all of the lab-scale work disclosed herein, tetrahydrofuran (THF) was used as the selected solvent, after comparing it with various other solvents. ZX is soluble (at varying levels, all of which are temperature-dependent) in a number of polar organic solvents, including cyclohexanone, chloroform, methylene chloride, and others. Any polar organic solvent (or any other solvent with suitable traits, which must include sufficiently high solubility of ZX at the temperatures involved, sufficiently high volatility levels to allow rapid evaporation and removal of the solvent from the ZX/oil mixture at the temperatures involved, etc.) can be evaluated for possible use during manufacturing-scale operations. The choice of a preferred solvent in a particular manufacturing operation will depend heavily on non-scientific factors, including: (i) economic factors, such as the cost of a solvent, the quantities needed, solvent loss and recovery rates, and processing times and temperatures needed for evaporating, removing, and recovering the solvent; (ii) safety factors, including toxicity, asphyxiation risk if a sizable leak occurs, carcinogenicity, and other medical risks that arise whenever a highly volatile solvent is used in a manufacturing operation; and, (ii) the detailed operating parameters (times, temperatures, etc.) that are involved in the specific steps that are settled upon during scale-up operations.

A relatively small quantity of water was added to the ZX/solvent mixture, and that mixture was loaded into a mixing vessel 140, shown in FIG. 2. Testing indicated that adding some quantity of water was important to the quality of the final product. Although the reasons why were not analyzed carefully, it was presumed that the presence of some water in the oily ZX mixture, during the evaporation process that occurred inside chamber 180, may have helped disrupt and impede the process of ZX crystal formation, thereby helping to prevent the ZX crystals from growing undesirably large.

Separately, an edible oil was mixed with an emulsifier. The oil/emulsifier mixture was also loaded into mixing vessel 140, where it was mixed with the ZX/solvent mixture. Because of its known health benefits, olive oil was used as the edible oil, in all tests disclosed herein. Any other type of edible oil (such as corn oil, canola oil, safflower oil, palm oil, or other vegetable oils, as well as various liquid oils derived from animals, such as fish oils or processed fats) can also be evaluated for use as described herein, if desired. Lecithin (a natural surfactant, commercially derived from eggs or soybeans) was used in all tests disclosed herein. Other emulsifiers (including various synthetic emulsifiers, such as "TWEEN") can also be evaluated, if desired.

The ratios of the two liquids (ZX/THF, and oil/lecithin) which are mixed together in mixing vessel 140 can be controlled, in a manner which will ultimately control the total dosage (weight) of ZX which will be loaded into a capsule of a certain size. For example, if capsules containing 10 mg of ZX in 500 mg of oil are being manufactured, this dosage of ZX can be controlled by controlling the quantity of ZX-containing liquid that is mixed with a given quantity of the oil/emulsifier liquid. The total weight or volume of the ZX-containing liquid which is used in this mixing step will, in turn, depend on the ratio of ZX to solvent in this liquid, which can also be easily controlled.

In the lab-scale tests disclosed herein, "batch processing" methods were used to load mixing vessel 140. During commercial manufacturing, continuous flow loading and mixing steps can be used, if desired.

Both of the two liquid components were initially mixed using magnetic stirrers; those mixing steps did not require extended mixing, and took only a minute or two. In the lab-scale tests disclosed herein, feed vessel 140 did not use an internal stirrer; however, if a stirrer inside a feed vessel is desired for commercial-scale manufacturing, it can be provided.

FIG. 2 also depicts gas supply cylinder 100. In the lab tests described herein, gas supply cylinder 100 was a refrigerated cylinder containing liquid nitrogen ($N_2$), which is readily available as a commodity chemical. When liquid $N_2$ (which must be kept under extremely cold conditions) evaporates, nitrogen gas is released. It is an inert gas; at the pressures and temperatures involved in the steps disclosed herein, it does not undergo any chemical reactions with ZX, or with any of the solvents, carriers, or other compounds used herein. Therefore, the use of nitrogen gas in the processing disclosed herein helped protect the ZX and the solvents from oxygen and oxidation.

Nitrogen gas emerged under pressure from gas supply cylinder 100, and passed through mixer gas line 110 using a control system that includes pressure valve 112. The gaseous nitrogen passed through a pressure manifold 120, which allowed each of two emerging gas streams to be controlled separately, at different pressures and quantities.

One of the nitrogen gas streams, which was carried by gas line 130, entered the mixing vessel 140, at a controllable pressure referred to herein as $P_{MIXER}$. This pressure, which was exerted on the upper liquid surface of the liquid inside mixing vessel 140, provided a controllable force which could be adjusted to control the rate at which the liquid mixture of ZX, solvent, oil, and emulsifier inside mixing vessel 140 was pumped out of the bottom of vessel 140, through control valve 142 and through liquid line 144, into an atomizer device 170.

The other nitrogen gas stream which emerged from pressure manifold 120 passed through atomizer gas line 160, at a controllable pressure referred to herein as $P_{SPRAY}$. The gas which passed through gas line 160 also entered the atomizer device 170.

The method which uses gas streams as propellants, as described herein, provided very good results in the laboratory-scale tests that have been carried out to date. However, alternate forms of pumping (including the use of mechanical pumps and/or entrainment equipment, and other mechanical devices having solvent-resistant liquid-contacting components) can be used, if desired, as this invention is scaled up to the needs of commercial manufacturing operations.

In addition, any type of high-shear and/or high-pressure mixer, sonicator, press, or other emulsification device (these devices are well-known and are used to manufacture emulsions for cosmetics, drugs, and other uses) can be tested, in conjunction with the equipment and methods described herein, to determine whether any such processing machine or processing step can further reduce the resulting particle sizes, or lead to other manufacturing or economic benefits (such as faster processing times, reduced solvent quantity requirements, reduced solvent mixing requirements, etc.), when used in combination with the techniques and equipment disclosed herein.

Figure 3:
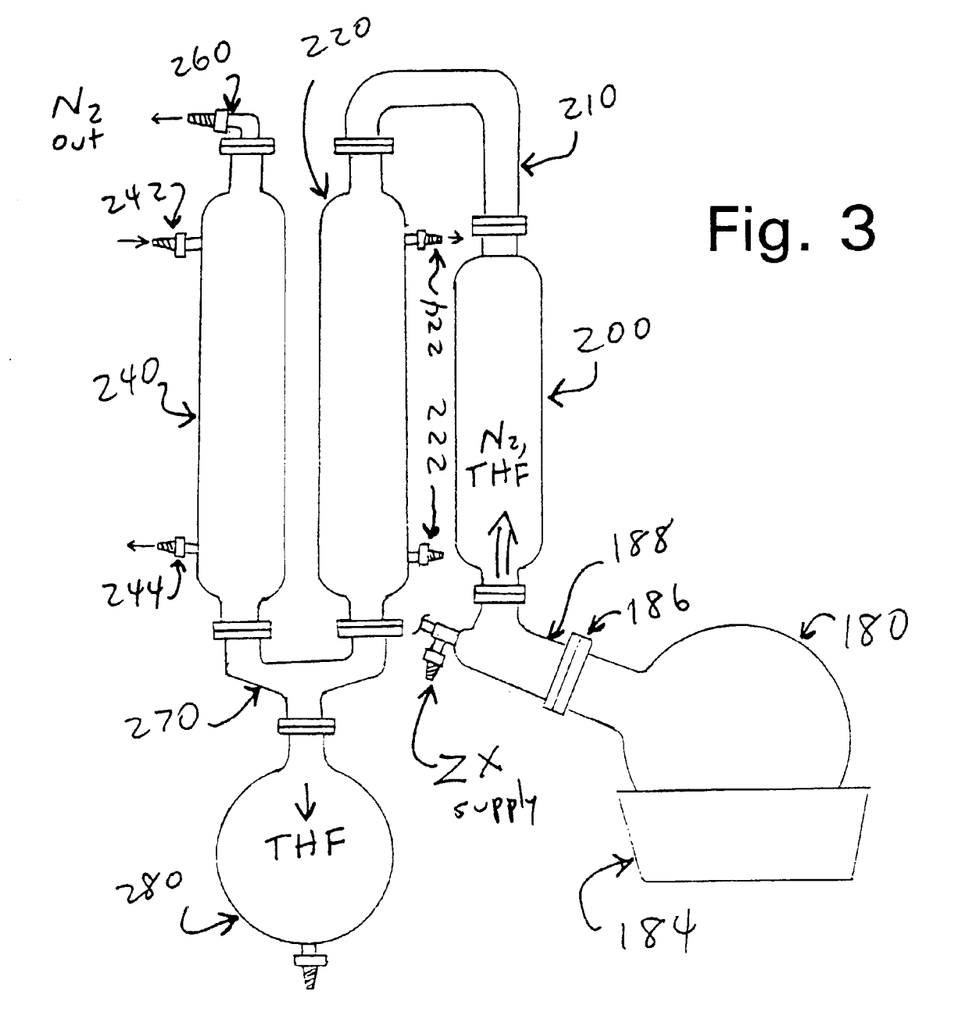

Similarly, as the processes here are scaled up to enable the manufacturing of commercial volumes, any of various other types of equipment can be evaluated for carrying out the processes disclosed herein. In particular, equipment selections which will allow continuous processing, rather than "batch" processing, will deserve evaluation. As one example, the mixing chamber 140 described herein might be replaced by a continuous-flow reaction chamber or vessel. As another example, the rotary evaporator chamber 180 might be replaced by a device which uses cooling coils, plates, baffles, or similar devices that are spaced apart from each other, to allow gases to flow between them; the atomizer nozzle will direct the mist into the flow-through condensation unit, and automated scrapers or similar devices can periodically wipe the condensate downward, off the surfaces of the condensing tubes or plates and into a collection tray.

Inside the atomizer device 170, the mixture of ZX, solvent, and oil stayed inside a segregated tube, which for most of its length was contained within the larger outer tubing of atomizer device 170. At a location near the atomizer nozzle 174, a short segment 172 of the liquid-carrying tubing emerged from the larger outer tubing of atomizer device 170; this exposed segment 172 provided easier access to the liquid-carrying tubing, for cleaning and unclogging purposes. The ZX/solvent/oil mixture carried by liquid line 144 and tubing segment 172 did not mix with the nitrogen gas carried by gas line 160, until they were combined just before they both emerged from atomizer nozzle 174.

The ZX-containing spray that emerged from atomizer nozzle 174 condensed on any solid surfaces it contacted, inside the spherical chamber 180 of a rotary evaporator. The THF solvent in the liquid that emerged from the atomizer nozzle evaporated almost immediately in the vacuum conditions maintained inside the chamber, and was not believed to be a substantial component of the "cream" which condensed on the interior walls of the chamber 180. As it evaporated, the THF solvent was carried out of the chamber 180, through "neck" 186 (shown in FIG. 3), by the continuous flow of nitrogen gas through chamber 180.

Rapid evaporation of the THF solvent is important in this invention, since crystals tend to grow larger over time. The growth of crystals over time can include: (i) accretion, in which additional molecules of the crystallizing compound fit precisely into a molecular "lattice" that is being formed around a single "condensation nucleus", to form larger unitary crystals; and, (ii) aggregation, in which discrete or semi-discrete crystals, initially started by separate condensation nuclei, tend to form clusters, clumps, and other aggregations.

Using a conventional drive mechanism as normally used on rotary evaporators, the spherical chamber 180 was rotated during the processing reaction, and the bottom surface of chamber 180 passed through a heated water bath 184, shown in FIG. 3. That heating process helped remove the water from the condensate.

After a number of trial-and-error tests had been completed, the operators developed a reliable ability to determine, using visual observations, when a suitable and appropriate amount of the deep-orange "cream" had condensed on the inner walls of the chamber 180. When that point was reached, the rotation of the chamber was stopped, and a vacuum was maintained for several minutes longer, to remove any additional THF solvent and water. After several minutes, the vacuum was release, the chamber was detached from the neck, and the "cream" condensate was collected with a flexible spatula, and analyzed.

In addition to indicating when a proper amount of cream had condensed on the walls of the chamber, visually monitoring also helped the operators ensure that proper gas pressures and flow rates are sustained in each of the supply lines 144 and 160, as mentioned above. In evaporating chambers used for manufacturing-scale operations, other types of automated and/or electronic monitoring systems can be used if desired.

The ability to separately and independently adjust the $P_{MIXER}$ and $P_{SPRAY}$ gas pressures, in lines 130 and 160, respectively, provided a highly useful and convenient way to control the final product quality, by controlling the spray output inside the rotary evaporator. Since the spherical chamber 180 was made of clear glass (of a "PYREX" type, which is resistant to chemicals and heat, and which does not expand or contract significantly when heated or cooled), the spray output which emerged from atomizer nozzle 174 inside chamber 180 could be visually watched and monitored. When the two gas pressure values ($P_{MIXER}$ and $P_{SPRAY}$) were kept in proper adjustment relative to each other, a steady and consistent fine mist with a slightly orange-yellow color emerged from the nozzle 170.

If the $P_{MIXER}$ pressure was too high, too much of the ZX/solvent/oil liquid was forced out of mixing vessel 140 and through the atomizer nozzle 174; this led to sputtering, nonhomogenous globs and jets of liquid, and similar problems, which could be seen and heard inside the glass chamber 180. In addition, if this condition occurred, it tended to saturate and/or overwhelm the evaporative capacity inside the chamber, thereby allowing the ZX crystals more time to form and grow larger.

By contrast, if the $P_{SPRAY}$ value was too high, not enough liquid was mixed with the gas that emerged from nozzle 174, and the resulting spray which collected on the glass walls of chamber 180 had a thin and watery appearance, without a sufficiently orange-yellow color. In addition, other problems sometimes arose if the $P_{SPRAY}$ value became too high. On some occasions, if the pressure inside the atomizing nozzle became too high, it caused the liquid flow to reverse, so that the ZX/oil/solvent mixture was driven back to the mixing vessel. On other occasions, excess spray pressure caused "overatomization" of the liquid inside the chamber, which tended to cause too much of the ZX-containing mist to pass through the chamber without condensing, and be carried into the solvent recovery system.

Accordingly, if either condition began to develop, the controls of pressure manifold 120 had to be adjusted, to bring the spray inside chamber 180 back into desired levels of viscosity and color. This was not difficult and could be accomplished quickly and easily, using the equipment described herein, simply by adjusting the $P_{MIXER}$ and/or $P_{SPRAY}$ gas pressures.

The fluid-handling properties of the liquids involved did not pose any significant problems. Only a relatively small quantity of ZX pigment was dissolved in a relatively large volume of THF, and THF is a very thin, non-viscous, highly volatile clear liquid. Therefore, even after the oil/emulsifier mixture was also added, the final mixtures, which contained a high percentage of THF, were thin and non-viscous, and flowed easily through the tubing that was used.

If a quantity of water was added to the ZX/solvent mixture, or to the ZX/solvent/oil mixture at any other step along the way, a water-removal step can be performed on the condensate, if desired. Various methods can be used for removing water from an oily mixture, as known to those skilled in the art.

Recovery of the $N_2$ gas and evaporated THF solvent which emerged from the spherical chamber 180 was carried out using the components depicted in FIG. 3. The rotating chamber 180 was coupled (via a "neck" or "collar" connector 186) to a non-rotating neck conduit 188. The emerging $N_2$ gas stream carrying evaporated THF passed through the neck conduit 188 and rose into an expansion chamber 200. It then passed through a conduit 210, and into a first condenser 220. Condenser 220 had internal coils that carried a refrigerated coolant; this coolant entered via inlet valve 222, and exited via outlet valve 224, in a "counter-flow" manner (i.e., the coolant travelled upward, while the condensing gases travelled downward). In the system used in the tests described herein, a second condenser 240 was also used, with counterflow coolant flow established by inlet valve 242 and outlet valve 244.

The nitrogen gas stream emerged via gas outlet 260, after travelling through both of the condensers 220 and 240. THF, which condensed into liquid inside both of the condensers 220 and 240, passed through collection manifold 270 and was collected in a refrigerated collection chamber 280. If desired, two collection chambers can be used, in parallel, so that either chamber can be shut down and emptied, when nearly full, while the other chamber continues to operate.

This system was used with very good results, in various trials. Typical mixing and reaction parameters which gave good results are disclosed in Example 2.

Bioavailability tests, which tested the resulting microcrystalline ZX preparations on human volunteers, are described in Examples 3 and 4. The results, which showed greatly enhanced bioavailability, are provided in Example 3 and Table 1.

Additional bioavailability tests, comparing the microcrystalline ZX preparations against a similarly processed microcrystalline lutein preparation, were also carried out on human volunteers, are described in Example 5. The results, although carried out on small sample sizes, indicated that microcrystalline ZX was taken up and deposited into the retinal more efficiently than similar microcrystalline lutein, as described in Table 2.

EXAMPLES

Example 1
Preparation of Lyophilized Coarse-Grain ZX Powder

Zeaxanthin (ZX) was synthesized by fermenting a culture of *Flavobacterium multivorum* cells, derived from the cell strain deposited with the American Type Culture Collection under ATCC accession number 55238. This fermentation used the methods disclosed in U.S. Pat. No. 5,854,015 (Garnett et al 1998), cited above and incorporated herein by reference.

In some test runs, the liquid broth was separated from the cells by centrifugation, before the processing described below. However, that step did not appear to make a major difference in the crystal sizes in the resulting products.

During all processing steps described below, any mixtures containing ZX were protected from light, heat, and oxygen.

Acetone was added to the cells, at various quantities which generally centered on 15 liters of acetone per gram of cell solids. This killed the cells and extracted the majority of the ZX into the liquid (solvent) phase. The cells were then placed in a filter press to remove the cell solids.

The acetone was evaporated from the liquid under warm conditions (about 33 to 43° C.), under a mild vacuum (typically ranging from 100 to 300 mbar, which is about 0.1 to 0.3 atmospheric pressure). The acetone was recycled. The oily residue contained ZX in large crystalline form. It also contained some water (which is miscible with acetone) and various other cell residues that are soluble in acetone.

Water was added at a weight ratio of 200 grams water per gram of ZX, and the mixture was processed using a standard mechanical mixer at 300 rpm for 15 minutes. The mixture was then loaded into a filter vessel, and forced through a Teflon filter with 5 to 20 µm pore size, at 15 psig pressure. The water passed through, and the ZX and various solids stayed on the filter.

The filter was washed with hexane, and the liquid that emerged from the filter was stirred and then forced through the Teflon filter again. The water and hexane passed through, allowing the hexane solvent to carry with it various impurities. The residue that remained on the filter contained ZX at a purity ranging from about 75% to about 90%, still in relatively large crystals.

The filter was then lifted out of the filter chamber and placed in a washing chamber, which had an outlet tube connected to a Biotage "Flash 75" chromatography chamber loaded with silica gel.

The filter was washed initially with a mixture of 95% hexane and 5% acetone, followed by a mixture of 90% hexane and 5% acetone, to remove various impurities that are soluble in hexane. Each time, the liquid filtrate that emerged was processed to recover the solvent, but was not otherwise used.

Subsequent washings used pure acetone; due to the small volume of the chromatography unit, these washings generally totalled 20 to 60 times the volume of the chromatography unit. During these steps, the acetone/ZX mixture which emerged from the loading chamber was passed through the silica gel column. Since ZX will not cling to silica as tightly as various other impurities will, the acetone solvent passing through the silica gel eluted the ZX from the gel, and a somewhat more pure acetone/ZX mixture emerged from the chromatography unit while various impurities remained inside the gel.

After the filtrate was collected, the acetone was removed by evaporation, typically at about 40° C. and about 200 mbar vacuum. The resulting ZX preparations were about 95 to 99% pure.

Water was then added at a weight ratio of 4:1, and the mixture was stirred using a magnetic stirrer at 300 rpm for 15 minutes. This created a suspension of ZX in water. This suspension was placed in a freezer at −20° C. until frozen solid. It was then lyophilized at −70° C. and less than 100 mbar until the water residue was reduced to about 3–4% by weight. This typically required about 24 hours for a 400 ml batch containing 100 grams of ZX.

The products which resulted from all of these types of batch preparations were free-flowing powders which remained in powdered form at room temperature. The relatively large and coarse crystals usually had average diameters ranging from about 10 microns up to about 100 microns.

Example 2

Treatment of Powdered ZX

Powdered lyophilized ZX, prepared as described in Example 1, was dissolved in tetrahydrofuran (THF), at concentrations up to 20 g of ZX per liter (which is close to the saturation level of ZX in THF, at the temperatures used). Selected concentrations depended on the target weight of ZX in each final capsule. Conventional orally-ingested capsules of the type that are used to hold Vitamin E in an oil-based formulation can hold up to about 600 mg (0.6 ml) of liquid. Accordingly, if the encapsulated liquid contains 10% ZX in an oily carrier comprising an edible oil (such as olive oil, corn oil or other vegetable oil, etc.), each capsule can contain up to about 60 mg ZX. Typical dosage ranges for the capsules developed as disclosed herein were about 1 to about 10 mg ZX per capsule. Typical capsules contained up to about 500 mg of the ZX-in-oil liquid.

A small amount of water (0.5% v/v) was added to the THF/ZX mixture. Separately, 6% w/w lecithin (an emulsifying agent) was added to olive oil.

The two mixtures (ZX in THF, and lecithin in oil) were then mixed together using a magnetic stirrer. Neither stirring operation required more than a few minutes.

The complete mixture was then placed into feed vessel 140, shown in FIG. 2. Nitrogen gas under about 7 to 10 psig pressure was also pumped into feed vessel 140. The resulting mixture was allowed to flow out of the feed vessel 140, through control valve 142, at a rate of about 11 ml per minute. Since a feed vessel with a conical outlet was used, the surface area of the upper liquid surface inside the feed vessel was roughly ten times higher than the pressure on the liquid passing through valve 142.

This mixture entered a 20-liter rotary evaporator, shown as device 180 in FIGS. 2 and 3, through a tubing system as illustrated in FIG. 2. At the same time, pressurized nitrogen gas was also being injected into the rotary evaporator, under a pressure of about 15 psig. The liquid and gas commingled as they passed through an atomizing nozzle and entered the chamber of the rotary evaporator, which was maintained at 40° C. by a water bath. The initial vacuum in the evaporator was about 100 mbar, before entry of the ZX and nitrogen streams; under steady flow conditions, the vacuum usually remained in a range of about 300 to 400 mbar. The THF evaporated completely inside the chamber, and was recovered and recycled, using the expansion chamber, condenser stack, and catch vessels illustrated in FIG. 3.

The ZX-oil mixture coated the inside of the rotary evaporator chamber, in the form of a "cream". When visual inspection indicated that this cream had reached an appropriate thickness, the rotary evaporator was stopped, and the "cream" was collected and put on dry ice to stabilize it. It was then lyophilized at −70° C. and less than 100 mbar, usually for about 8 hours, to remove any remaining water or THF.

When this final product (with micro-crystalline ZX suspended in olive oil) was warmed up, it was ready to be loaded directly into capsules for oral ingestion. Average particle sizes of the ZX in this oily carrier liquid ranged from about 0.2 to about 2 $\mu$m.

Example 3

Bioavailability of Beadlet vs. Micro-Crystalline ZX

An initial set of bioavailability tests, comparing beadlet ZX versus micro-crystalline ZX, was carried out on a single human volunteer, in order to establish suitable test dosages, response times, and other parameters for a larger set of bioavailability tests on a substantially larger population of volunteers. However, the tests on the first volunteer required literally dozens of "needlesticks" (i.e., skin and vein punctures, using hypodermic needles), in order to draw blood samples that could be chemically analyzed for concentrations of ZX and other carotenoids. Each needlestick generated discomfort, as well as risks of infection, and of long-term damage to the blood vessels being punctured.

An inordinately large number of needlesticks was required, in order to fully establish ZX and other carotenoid concentrations in the blood over five different time periods, which were: (1) "baseline" levels, prior to any treatment; (2) the first period, while the volunteer was ingesting a preparation containing ZX in beadlet form; (3) a "cleanout and return to baseline" period, after the first (beadlet) treatment ended, before the second (micro-crystalline) treatment could begin; (4) the second treatment period, using micro-crystalline ZX; and, (5) a final post-treatment period, as concentrations returned to baseline levels. It should also be recognized that, during each of these five spans of time, multiple needlesticks were required, for two reasons: (i) to obtain statistically useful data on the variability of ZX concentrations (expressible in conventional statistical terms, such as standard deviation, or standard error of the mean) on different days, during a certain baseline level or treatment regimen; and, (ii) to obtain useful data on time-dependent increases or decreases in ZX concentrations in the blood, after a treatment regimen began, was changed, or ended.

By the end of the complete set of tests on the first volunteer, it had become quite apparent that the micro-crystalline ZX preparation had outperformed the beadlet ZX preparation by a wide margin. The results are provided in Table 1. Briefly, when this individual ingested ZX in a "beadlet" preparation (prepared by the lyophilization method described in Example 1) for 35 successive days, at dosages of 20.75 mg ZX per day, the ZX content in his blood serum increased to a supplemented level of 0.101 $\mu$g/ml. This concentration was about 2.5 times higher than his baseline level, 0.039 $\mu$g/ml.

By comparison, when this same individual ingested ZX at a closely similar dosage (21.5 mg/day), but in microcrystalline form rather than beadlets, his blood serum levels initially increased to 0.549 $\mu$g/ml, after 7 days. That concentration is more than 14 times higher than his baseline levels, and it is more than 5 times higher than his highest measured level, when he was taking the beadlet preparation.

After 14 days, his blood serum concentration levelled off at 0.440 $\mu$g/ml. That is more than 11 times higher than his baseline levels, and it was more than 4 times higher than his highest measured level while he was taking the beadlet preparation.

When it became clear that the micro-crystalline ZX had performed so much better than the beadlet ZX in that set of tests, there was no enthusiasm or even interest among any of the other volunteers for enduring an large and truly daunting number of needlesticks. All the other volunteers were entirely willing to be tested using microcrystalline ZX, and were also willing to undergo comparative testing of microcrystalline ZX against commercial preparations of other carotenoids, as described in Example 4. However, after seeing the abundantly clear results from the first volunteer, none of the other volunteers wanted to go through a lengthy and extensive testing process, requiring dozens of needlesticks, to compare beadlet ZX against microcrystalline ZX, merely to demonstrate something that, in their opinion, had already been demonstrated and proven.

Accordingly, only one volunteer was fully evaluated using a regimen of coarse-grained ZX, followed by a delay for restabilization and return to baseline, followed by a regimen of microcrystalline ZX. The data from those tests are in Table 1.

Table 1—Results of DG Blood Concentrations

Example 4

Comparisons with Other Commercial Preparations

Additional tests on human volunteers were done, to compare the micro-crystalline ZX preparation to two different commercially available preparations of lutein (another carotenoid which is an isomer of ZX, and which has an almost-identical chemical structure). When a beadlet preparation of lutein (purchased from Kemin Company, Des Moines, Iowa) was ingested at a dosage of 20 mg/day for 13 days, blood serum concentrations increased to an average of about 1.5 times higher than baseline values. This value was comparable to the doubling of ZX concentrations that were commonly seen when beadlet ZX preparations were ingested for 14 days.

By contrast, as noted in Example 3, when microcrystalline ZX was ingested for 14 days, ZX levels in blood serum increased to more than 11 times higher than baseline levels.

In yet another test, a commercially available preparation of lutein in an oil carrier (also purchased from Kemin Company, Des Moines, Iowa) was taken at a dosage of 20 mg/day, for 13 days. This oil-carrier formulation performed better than the beadlet preparation, and increased lutein levels to about 5 times higher than baseline levels.

However, as noted above, the microcrystalline ZX formulation performed at better than twice that level of efficacy, and established an 11-fold increase in blood serum concentrations.

Example 5

Comparison with Microcrystalline Lutein

Still other tests were on human volunteers, to compare the processed nano-particle zeaxanthin formulation, prepared as described above, against a nano-particle lutein formulation. The nano-particle lutein formulation was prepared, starting with commercially available lutein (purchased from Kemin Corporation, Des Moines, Iowa) suspended in oil, and processed using the same steps disclosed herein. Microscopic analysis indicated that the particle sizes of the processed lutein were comparable to the particle sizes of the nano-particle zeaxanthin.

Fifteen healthy adult volunteers were divided into groups, and each group was given capsules containing 10 mg of either zeaxanthin or lutein. The capsules were taken twice daily, for a total of 20 mg/day. Total administration lasted for 180 or 190 days.

Before the trials began (i.e., at Day 0, which provided baseline data), and at various intervals during the 180 day test period, healthy adult volunteers were tested for concentrations of zeaxanthin, lutein, and various other carotenoids in their blood serum. Serum samples were shipped on ice via overnight courier, to an independent lab, Craft Technologies, Inc. (Wilson, N.C.), for analysis.

Unlike the macular pigment densities measured by flicker photometry (discussed below), measurements of zeaxanthin or lutein concentrations in blood serum did not result in any apparent anomalies. All volunteers who ingested one or the other showed entirely reasonable and expectable responses. The values are provided below, in Table 2.

TABLE 2

BLOOD SERUM CONCENTRATIONS OF ZX OR LUTEIN IN RESPONSE TO SUPPLEMENTS

|  | Lutein | Zeaxanthin |
| --- | --- | --- |
| Day 0 | 0.1224 ± .035 | 0.0496 ± .022 |
| Day 1 | 0.1641 ± .031 | 0.0764 ± .002 |
| Day 3 | 0.2644 ± .103 | 0.1544 ± .022 |
| Day 10 | 0.3620 ± .057 | 0.2782 ± .022 |
| Day 40 | 0.3222 ± .172 | 0.2483 ± .153 |
| Day 180 | 0.3155 ± .123 | 0.3217 ± .093 |

Statistical significance (95%) was reached by Day 1 for both carotenoids; by Day 180, probability levels were at $P<0.0001$.

The numbers in Table 2 indicate three things. First, baseline levels of zeaxanthin, in blood serum, are significantly lower than baseline levels of lutein. This is not surprising, since lutein is the dominant carotenoid, and is present in much greater abundance than zeaxanthin in most food sources.

The second finding centers around the fact that zeaxanthin concentrations were increased, on a relative basis, by a much larger amount than lutein concentrations. By Day 10, ZX levels increased to more than 5.6-fold higher than the baseline; by contrast, the lutein increase was less than 3-fold. By Day 180, ZX levels increased to 6.48-fold higher than baseline, while lutein levels were 2.57-fold higher.

In addition, unlike lutein concentrations, which appeared to reach a saturation value by about Day 10, zeaxanthin concentrations either (i) never reached saturation, or (ii) if they did reach saturation, it did not occur until after Day 40.

However, it should also be recognized that zeaxanthin and lutein concentrations both appeared to reach roughly the same values, in a range of between 0.3 and 0.4 micrograms per milliliter.

Macular pigment density was also tested, using heterochromatic flicker photometry. These tests, carried out by a trained ophthalmologist, compared the optical density of the macular pigment at a position 1° from the foveal center, against the optical density of the pigment at 5° from the foveal center.

It should be recognized that flicker photometry measurements, which were developed some time ago and which can be done using machines that are relatively common, rely on several assumptions that do not hold true for everyone. In particular, since these measurements use readings at the 5° position as a baseline for comparison, they assume there is little or no macular pigment at the 5° position; however, this is not true for all patients. For this and other reasons, flicker photometry is not especially accurate, and measurements obtained from it should be regarded as rough estimates, rather than precise figures.

More accurate machines and methods have been developed recently, including spectral fundus reflectometers, and scanning laser ophthalmoscopes; although these machines are relatively rare and quite expensive, they provide significantly better and more accurate and reliable results. Berendschot et al 1999 (supra) reported that in a comparison of three different methods, using a single set of volunteers as test subjects, laser mapping resulted in variances of 10%, spectral fundus reflectance resulted in variances of 17%, and flicker photometry resulted in variances of 71%.

With those caveats, some of the results that arose from the macular pigment density measurements included the following:

A. In both treatment groups, some people clearly responded; their macular pigment density (measured by comparing 1° flicker photometry values against 5° values) clearly increased.

B. However, in both groups, other people apparently did not respond, and showed no measured increase in their macular pigment density. This was anomalous, and could not be explained except possibly as an artifact of the flicker photometry measurement technique that was used.

C. The portion of responders in the zeaxanthin supplement group (5 out of 8 volunteers) was clearly higher than in the lutein supplement group (only 2 out of 7 volunteers).

D. People who started out with relatively low baseline levels of macular pigment were more likely to respond by showing significant increases in macular pigment after they began taking supplements.

Thus, there has been shown and described a new and useful manufacturing process for creating micro-crystalline zeaxanthin (and other carotenoids) with substantially improved levels of bioavailability. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

What is claimed is:

1. A method of creating a microcrystalline carotenoid preparation for oral ingestion, comprising the following steps:
   a. mixing a selected carotenoid in a suitable selected non-aqueous solvent, to create a solvent-carotenoid liquid mixture;
   b. mixing the solvent-carotenoid liquid mixture with an oily carrier liquid that is non-toxic and orally ingestible, thereby creating a solvent-carotenoid-carrier liquid mixture;
   c. passing the solvent-carotenoid-carrier liquid mixture and a stream of inert gas through a spray nozzle causing a mist to emerge, said mist contacting one or more solid surfaces designed for condensate collection, in a manner which (i) causes the mist to form a liquified condensate which can be collected, and (ii) allows the gas and the solvent to be removed from the liquified condensate,
   wherein the liquified condensate contains the selected carotenoid in a form having average particle sizes less than about 10 microns, in an oily carrier liquid.

2. The method of claim 1 wherein the carotenoid is selected from the group consisting of zeaxanthin, lutein, beta-carotene, lycopene, and astaxanthin.

3. The method of claim 1, wherein the solvent is selected from the group consisting of tetrahydrofuran, acetone, ethanol, and ethyl acetate.

4. The method of claim 1 wherein water is added to the solvent-carotenoid mixture, and wherein the product which remains after inert gas entrainment and removal is dried by an additional processing step to remove water from the product.

5. A carotenoid preparation containing a selected carotenoid in a form having average particle sizes less than about 4 microns in diameter, prepared by the method of claim 1.

6. A carotenoid preparation of claim 5, wherein the carotenoid is selected from the group consisting of zeaxanthin, lutein, beta-carotene, lycopene, and astaxanthin.

7. A carotenoid preparation containing zeaxanthin in a form having average particle sizes less than about 4 microns in diameter, suspended directly in an edible oily carrier substance.

8. The carotenoid preparation of claim 7, wherein the oily carrier substance comprises a vegetable oil.

9. The carotenoid preparation of claim 7, wherein the vegetable oil is selected from the group consisting of olive oil, corn oil, canola oil, safflower oil, and palm oil.

10. The carotenoid preparation of claim 7, wherein the oily carrier substance comprises a fish oil.

* * * * *